United States Patent [19]

Oda et al.

[11] Patent Number: 4,914,097
[45] Date of Patent: Apr. 3, 1990

[54] N-INDANYL CARBOXAMIDE DERIVATIVE AND AGRICULTURAL/HORTICULTURAL FUNGICIDE CONTAINING THE DERIVATIVE AS ACTIVE INGREDIENT

[75] Inventors: Masatsugu Oda; Toshiro Sakaki, both of Yokohama; Naoko Sasaki, Machida; Hirofumi Tomita, Machida; Nobuyuki Nonaka, Yokohama, all of Japan

[73] Assignee: Mitsubishi Kasei Corporation, Tokyo, Japan

[21] Appl. No.: 159,277

[22] Filed: Feb. 23, 1988

[30] Foreign Application Priority Data

Feb. 25, 1987 [JP] Japan .................... 62-42136
Apr. 16, 1987 [JP] Japan .................... 62-93799
Oct. 16, 1987 [JP] Japan .................... 62-261131
Oct. 16, 1987 [JP] Japan .................... 62-261132

[51] Int. Cl.$^4$ .................... A61K 31/495; C07D 241/14
[52] U.S. Cl. .................... 514/255; 514/361; 514/369; 514/370; 514/371; 514/372; 514/471; 544/406; 548/127; 548/196; 548/200; 548/214; 549/487
[58] Field of Search .................... 544/406; 71/92; 514/255

[56] References Cited

U.S. PATENT DOCUMENTS 4,511,581  4/1985  Ohsumi et al. .................... 514/617
4,608,385  8/1986  Noguchi et al. .................... 514/447

FOREIGN PATENT DOCUMENTS 873888    6/1971   Canada .
086111    8/1983   European Pat. Off. .
276177    7/1988   European Pat. Off. ............ 548/200
1695968  12/1970   Fed. Rep. of Germany .
1768686   5/1971   Fed. Rep. of Germany .
2132392   1/1973   Fed. Rep. of Germany .
2409011   9/1974   Fed. Rep. of Germany .
2701091   7/1977   Fed. Rep. of Germany .
2728523   1/1979   Fed. Rep. of Germany .
2922292   2/1980   Fed. Rep. of Germany .
56-57776  5/1981   Japan .
1302410   1/1973   United Kingdom .
8602641   5/1986   World Int. Prop. O. .

OTHER PUBLICATIONS

Clark, Michael Lawler, CA92-210186r (1980) "Fungicidal Compositions Containing Furan-3-Carboxamide".
Kumiai Chem. Industry Co., Ltd., CA96-20090q (1982) "Fungicidal 5-Thiazole Cardoxamilides".
Noguchi et al., CA99-122063n (1983) "Fungicidal N-Phenylcarbamates".
Ohsumi et al., CA100-85434a (1984) "A Fungicidal Indanylbenzamide".
Nishida et al., CA109-144598t (1988) "N-4-Indanylfuran, Thiophene, and 1H-Pyrrolecarboxamides ...".
Ohsumi et al., CA110-8205f (1989) "Preparation and Testing of Thiazolyl-and Pyrazolye ...".
Oda et al., CA110-75466e (1989) "N-Indanyl-heterocyclyl Carboxamide Derivatives ...".

Primary Examiner—Mukund J. Shah
Assistant Examiner—Cecilia Shen
Attorney, Agent, or Firm—Oblon, Spivak, McClelland, Maier & Neustadt

[57]  ABSTRACT

Disclosed herein is an N-indanyl carboxamide derivative as a novel compound, represented by the following general formula (I):

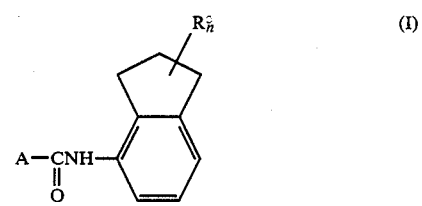

wherein A represents a group of the formula,

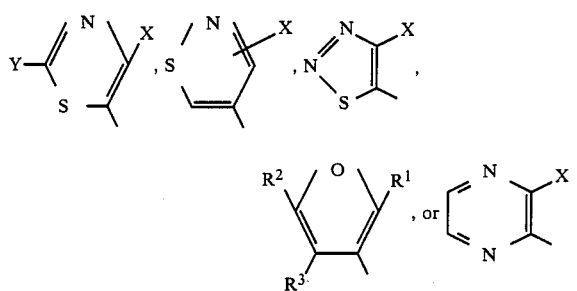

represents a halogen atom, a methyl group, or a trifluoromethyl group, Y represents a hydrogen atom, a halogen atom, a lower alkyl group, an amino group, a mercapto group, or a lower alkylthio group, $R^1$ represents a methyl group or a trifluoromethyl group, and $R^2$ and $R^3$ independently represents a hydrogen atom or a methyl group), R represents a lower alkyl group, and n is an integer in the range of 1 to 6, and an agricultural/horticultural fungicide comprising said N-indanyl carboxamide derivative as an active ingredient.

2 Claims, No Drawings

N-INDANYL CARBOXAMIDE DERIVATIVE AND AGRICULTURAL/HORTICULTURAL FUNGICIDE CONTAINING THE DERIVATIVE AS ACTIVE INGREDIENT

BACKGROUND OF THE INVENTION

The present invention relates to an N-indanyl carboxamide derivative and an agricultural/horticultural fungicide containing the derivative as an active ingredient. More in detail, the present invention relates to an N-indanyl carboxamide derivative represented by the following general formula (I):

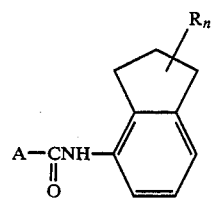

wherein A represents a group of the formula,

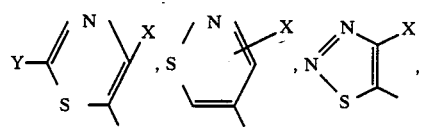

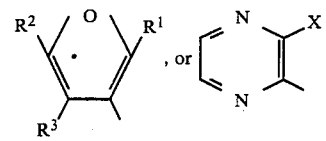

(wherein X represents a halogen atom, a methyl group, or a trifluoromethyl group, Y represents a hydrogen atom, a halogen atom, a lower alkyl group, an amino group, a mercapto group, or a lower alkylthio group, $R^1$ represents a methyl group or a trifluoromethyl group, and $R^2$ and $R^3$ independently represents a hydrogen atom or a methyl group), R represents a lower alkyl group, and n is an integer of 1 to 6, and an agricultural/horticultural fungicide, comprising as an active ingredient an N-indanyl carboxamide derivative represented by the following general formula (I):

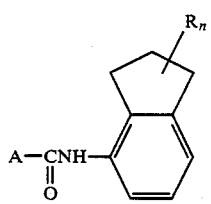

wherein A represents a group of the formula,

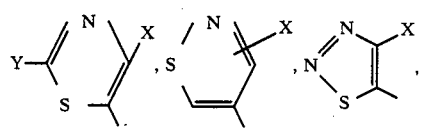

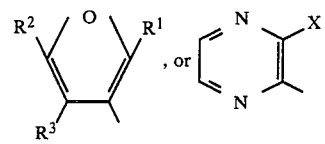

(wherein X represents a halogen atom, a methyl group, or a trifluoromethyl group, Y represents a hydrogen atom, a halogen atom, a lower alkyl group, an amino group, a mercapto group, or a lower alkylthio group, $R^1$ represents a methyl group or a trifluoromethyl group, and $R^2$ and $R^3$ independently represents a hydrogen atom or a methyl group), R represents a lower alkyl group, and n represents an integer in the range of 1 to 6.

It has been known that certain carboxamide derivatives have fungicidal activity and other similar biological activities. For example, such compounds as:

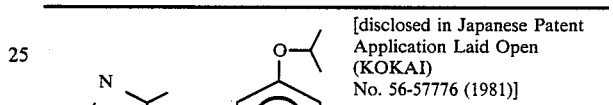
[disclosed in Japanese Patent Application Laid Open (KOKAI) No. 56-57776 (1981)]

(disclosed in Canadian Patent No. 873,888)

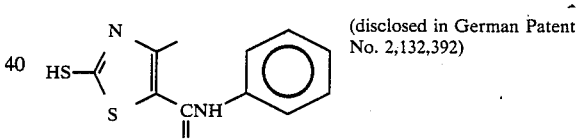
(disclosed in German Patent No. 2,132,392)

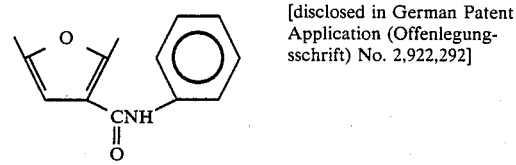
[disclosed in German Patent Application (Offenlegungsschrift) No. 2,922,292]

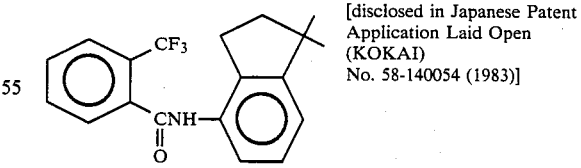
[disclosed in Japanese Patent Application Laid Open (KOKAI) No. 58-140054 (1983)]

have been demonstrated.

As shown from biological test examples mentioned later, however, these compounds have not necessarily sufficiently activity as agricultural/horticultural fungicides.

Benzimidazole-thiophanate fungicides such as benomyl-[methyl-1-(butylcarbamoyl)benzimidazol-2-yl-carbamate] and thiophanate methyl[1,2-bis(3-methoxy -carbonyl-2-thioureido)benzene] exhibited outstanding effects in preventing various pathogenic fungi which infest agricultural and horticultural produces and had been popularly used in the form of agricultural/horticultural fungicides since the 1970's. In this while, however, pathogenic fungi capable of exhibiting tolerance for these fungicides (hereinafter referred to as "drug-resistant strains") have spread out widely. Thus, there are times when these fungicides prove to be substantially unusable.

Cyclic imide fungicides such as purosimidone [N-(3,5-dichlorophenyl)-1,2-dimethylcyclopropane-1,2-dicarboxyimide] exhibited activity against such drug-resistant gray mold germ (Botrylis cinerea) and has found extensive utility as a substitute for the aforementioned benzimidazole-thiophanate fungicides. In recent years, however, resistant strains to these cyclic imide fungicides have appeared. In fact, they have often failed to prove to be usable in the field.

The N-phenyl carbamate compounds disclosed as in Japanese Patent Application Laid Open (KOKAI) No. 58-126856 (1983) have been reported as exhibiting high activity in controlling such drug-resistant strains as mentioned above. The N-phenyl carbamate compounds, however, exhibit entirely no effect in controlling drug-sensitive strains to benzimidazole or thiophanate fungicides. So that they do not fit independent use at times.

As a result of the inventors' diligent study in order to solve the various problems mentioned above, it has been found that an N-indanyl carboxamide derivative represented by the following general formula (I):

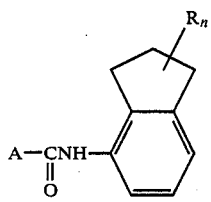

wherein A represents a group of the formula,

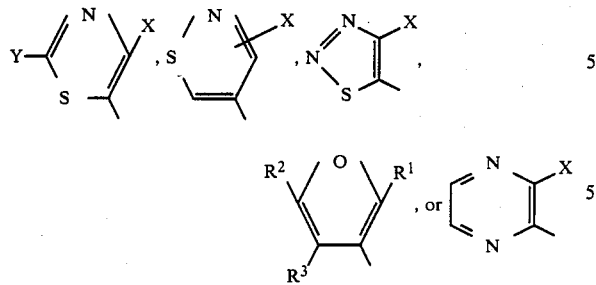

(wherein X represents a halogen atom, a methyl group, or a trifluoromethyl group, Y represents a hydrogen atom, a halogen atom, a lower alkyl group, an amino group, a mercapto group, or a lower alkylthio group, $R^1$ represents a methyl group or a trifluoromethyl group, and $R^2$ and $R^3$ independently represents a hydrogen atom or a methyl group), R represents a lower alkyl group, and n is an integer of 1 to 6, shows highly effective in controlling not only drug-sensitive strains but also drug-resistant strains. The present invention has been attained on the basis of the finding.

SUMMARY OF THE INVENTION:

In a first aspect of the present invention, there is provided an N-indanyl carboxamide derivative represented by the following general formula (I):

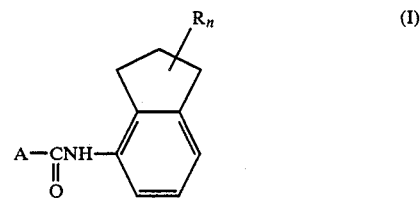

wherein A represents a group of the formula,

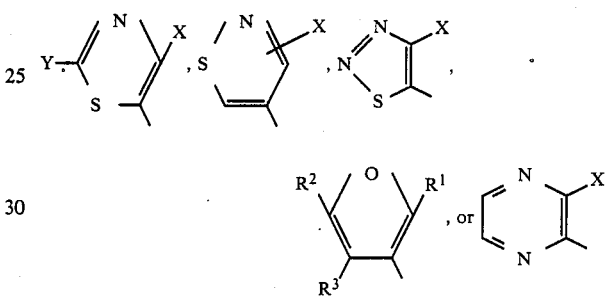

(wherein X represents a halogen atom, a methyl group, or a trifluoromethyl group, Y represents a hydrogen atom, a halogen atom, a lower alkyl group, an amino group, a mercapto group, or a lower alkylthio group, $R^1$ represents a methyl group or a trifluoromethyl group, and $R^2$ and $R^3$ independently represents a hydrogen atom or a methyl group), R represents a lower alkyl group, and n is an integer of 1 to 6.

In a second aspect of the present invention, there is provided an agricultural/horticultural fungicide, comprising as an active ingredient an N-indanyl carboxamide derivative represented by the following general formula (I):

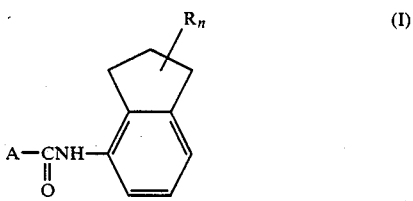

wherein A represents a group of the formula,

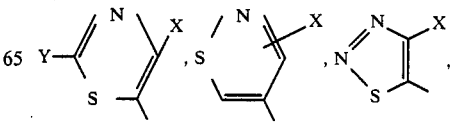

-continued

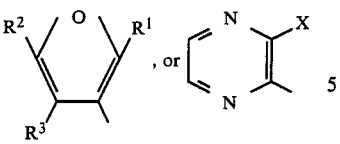

(wherein X represents a halogen atom, a methyl group, or a trifluoromethyl group, Y represents a hydrogen atom, a halogen atom, a lower alkyl group, an amino group, a mercapto group, or a lower alkylthio group, $R^1$ represents a methyl group or a trifluoromethyl group, and $R^2$ and $R^3$ independently represents a hydrogen atom or a methyl group), R represents a lower alkyl group, and n represents an integer in the range of 1 to 6.

DETAILED DESCRIPTION OF THE INVENTION

Specifically, the essence of the present invention lies in an N-indanyl carboxamide derivative represented by the following general formula (I):

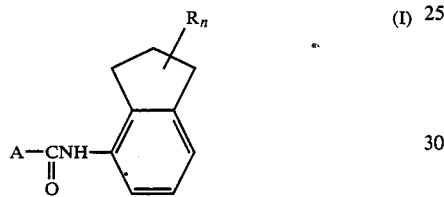

wherein A represents a group of the formula,

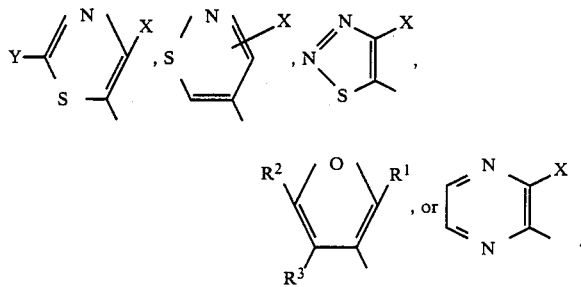

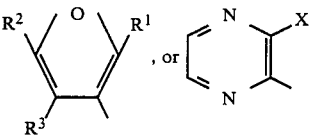

(wherein X represents a halogen atom, a methyl group, or a trifluoromethyl group, Y represents a hydrogen atom, a halogen atom, a lower alkyl group, an amino group, a mercapto group, or a lower alkylthio group, $R^1$ represents a methyl group or a trifluoromethyl group, and $R^2$ and $R^3$ independently represents a hydrogen atom or a methyl group), R represents a lower alkyl group, and n is an integer of 1 to 6 and an agricultural/horticultural fungicide containing the N-indanyl carboxamide derivative as an active ingredient.

The compounds of the present invention are represented by the general formula (I). In the general formula (I), A represents a group of the formula,

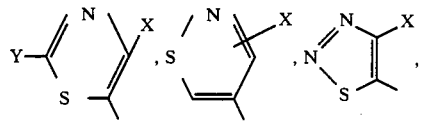

-continued

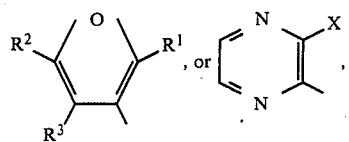

preferably 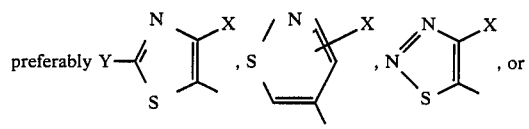

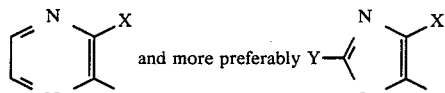 and more preferably 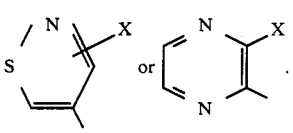

In the formulas indicated above, X represents a halogen atom, a methyl group, or a trifluoromethyl group and Y represents a hydrogen atom, a halogen atom, a lower alkyl group (preferably $C_1$-$C_4$ alkyl group), an amino group, a mercapto group, or a lower alkylthio group (preferably $C_1$-$C_4$ alkyl group). Preferably Y represents a hydrogen atom, halogen atom, a lower alkyl group (preferably $C_1$-$C_4$ alkyl group), or an amino group. More preferably Y represents a hydrogen atom, a lower alkyl group (preferably $C_1$-$C_4$ alkyl group), or an amino group, and most preferably a hydrogen atom or a lower alkyl group (preferably $C_1$-$C_4$ alkyl group). As the lower alkyl group, methyl group is most preferable.

In the formulas, $R^1$ represents a methyl group or a trifluoromethyl group, preferably a methyl group, and $R^2$ and $R^3$ independently represents a hydrogen atom or a methyl group. Preferably $R^3$ represents a hydrogen atom.

In the general formula (I), R represents a lower alkyl group, preferably a lower alkyl group having 1 to 3 carbon atoms, and more preferably a methyl group, and n is an integer of 1 to 6, preferably 1 to 4. Where n is an integer of 2 to 6, the plurality of R's may be equal to or different from each other.

Concrete examples of the compounds of the present invention represented by the general formula (I) are enumerated in Table 1 to Table 3. The compounds of the general formula (I) are not limited to these examples.

TABLE 1

(Structure: thiazole with Y-S, X, and amide linked to indane bearing R¹–R⁶)

| X | Y | R¹ | R² | R³ | R⁴ | R⁵ | R⁶ |
|---|---|---|---|---|---|---|---|
| CF₃ | CH₃ | H | CH₃ | H | C₂H₅ | CH₃ | H |
| Cl | NH₂ | CH₃ | H | CH₃ | H | CH₃ | CH₃ |
| Br | C₂H₅ | H | H | H | H | H | H |
| CH₃ | Cl | H | H | H | H | CH₃ | CH₃ |
| Cl | Cl | i-C₃H₇ | H | H | C₂H₅ | CH₃ | C₂H₃ |
| F | CH₃ | CH₃ | H | H | H | CH₃ | H |
| CH₃ | NH₂ | H | C₂H₅ | H | H | C₂H₅ | H |
| CF₃ | i-C₃H₇ | CH₃ | CH₃ | CH₃ | H | C₂H₅ | H |
| Br | Br | CH₃ | H | H | H | H | H |
| Cl | CH₃ | H | H | H | H | CH₃ | H |
| CH₃ | NH₂ | H | H | i-C₃H₇ | H | C₂H₅ | H |
| CH₃ | H | H | H | H | H | CH₃ | CH₃ |
| CH₃ | SH | H | H | H | H | CH₃ | CH₃ |
| CH₃ | H | CH₃ | H | H | H | CH₃ | CH₃ |
| CH₃ | SH | CH₃ | H | H | H | CH₃ | CH₃ |
| CH₃ | SCH₃ | H | CH₃ | H | H | CH₃ | CH₃ |
| CF₃ | CH₃ | CH₃ | H | H | H | CH₃ | CH₃ |

TABLE 2

(Structure: pyrazine with X, amide linked to indane bearing R¹–R⁶)

| X | R¹ | R² | R³ | R⁴ | R⁵ | R⁶ |
|---|---|---|---|---|---|---|
| F | CH₃ | H | H | H | H | H |
| Cl | H | C₂H₅ | H | H | H | H |
| Br | H | H | i-C₃H₇ | H | H | H |
| CH₃ | H | H | H | n-C₄H₉ | H | H |
| CF₃ | H | H | H | H | CH₃ | H |
| Cl | H | H | H | H | H | CH₃ |
| CF₃ | CH₃ | H | H | H | CH₃ | H |
| Cl | CH₃ | H | H | H | CH₃ | CH₃ |
| CF₃ | H | H | H | H | CH₃ | CH₃ |
| Br | H | CH₃ | H | H | CH₃ | CH₃ |
| CH₃ | H | H | CH₃ | H | H | H |

TABLE 3

(Structure: A—C(=O)NH— linked to indane bearing R¹–R⁶)

| A | R¹ | R² | R³ | R⁴ | R⁵ | R⁶ |
|---|---|---|---|---|---|---|
| isothiazole-3-CH₃ (4-methyl) | CH₃ | H | H | H | CH₃ | CH₃ |
| isothiazole-3-Cl (4-methyl) | H | C₂H₅ | H | H | CH₃ | H |
| 1,2,3-thiadiazole-4-CH₃ | H | H | CH₃ | H | H | H |
| 1,2,3-thiadiazole-4-CF₃ | CH₃ | H | H | H | CH₃ | CH₃ |
| furan-2-CH₃ (3-methyl) | CH₃ | H | H | H | CH₃ | CH₃ |
| furan-2-CH₃ (3-methyl) | H | H | H | H | CH₃ | CH₃ |
| furan-2-CH₃ (3-methyl, 5-CH₃) | CH₃ | H | H | H | H | H |
| furan-2-CH₃ (3-methyl, 5-CH₃) | CH₃ | H | H | H | CH₃ | CH₃ |
| furan-2-CF₃ (3-methyl) | CH₃ | H | H | H | CH₃ | CH₃ |
| furan-2-CF₃ (3-methyl) | H | H | H | H | CH₃ | CH₃ |
| furan-2-CF₃ (3-methyl, 5-CH₃) | H | H | H | H | CH₃ | CH₃ |

The compounds of the present invention are all novel and may be synthesized, for instance, according to the following reaction route:

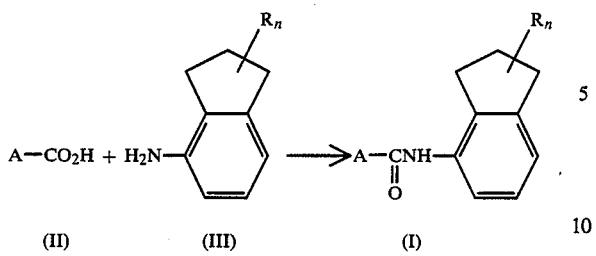

(II)   (III)   (I)

[wherein A, R and n have the same meanings as defined above]

As indicated by the reaction route, a carboxylic acid or a reactive derivative thereof represented by the general formula (II) is reacted with an amino-indane derivative represented by the general formula (III) in the presence or absence of an inert solvent for the reaction.

In the reaction, the carboxylic acid or reactive derivative thereof represented by the general formula (II) is used in an amount in the range of 0.5 to 1.5 equivalent, preferably 0.9 to 1.1 equivalent based on the amount of the amino-indane derivative represented by the general formula (III). This reaction can be carried out at a temperature in the range of from −70° C. to the boiling point of the solvent used therein, preferably from −40° C. to the boiling point of the solvent.

As examples of the carboxylic acid or reactive derivative represented by the general formula (II), corresponding carboxylic acids, acid anhydrides, acid chlorides and other similar acid halogenides, and carboxylic esters may be exemplified.

As examples of the solvent usable in the reaction, aromatic hydrocarbons such as benzene and toluene; halogenated hydrocarbons such as carbon tetrachloride and chloroform; aromatic halogenated hydrocarbons such as chlorobenzene; ethers such as diethyl ether, tetrahydrofuran, and dioxane; esters such as ethyl acetate; and polar solvents such as dimethyl sulfoxide, dimethyl formamide, and water may be exemplified.

In order for this reaction to proceed smoothly, it may use a reaction auxiliary in accordance with the kind of the carboxylic acid or reactive derivative thereof represented by the general formula (II).

As examples of the reaction auxiliary usable for the purpose, dehydrating agents such as ethoxyacetylene, dicyclohexyl carbodiimide and phosphorus pentoxide may be exemplified in the case where a carboxylic acid is used as (II); tertiary amines such as N-methyl morpholine and triethylamine, and aromatic bases such as pyridine, picoline and N,N-diethyl aniline may be exemplified in the case where an acid anhydride is used as (II), tertiary amines such as triethylamine, aromatic bases such as pyridine and picoline, alkalimetal hydroxides such as sodium hydroxide and potassium hydroxide, alkali metal hydrides such as sodium hydride, and alkali metal alcoholates such as sodium ethylate may be exemplified in the case where an acid halogenide is used as (II); and alkali metal alcoholates such as sodium ethylate may be exemplified in the case where a carboxylic ester is used as (II).

Such a reaction auxiliary can be used in an amount generally in the range of 0.01 to 2.0 equivalent, preferably 0.9 to 1.1 equivalent based on the amount of the aminoindane derivative represented by the general formula (III).

The compounds of the present invention can be otherwise produced by the following rearrangement reaction.

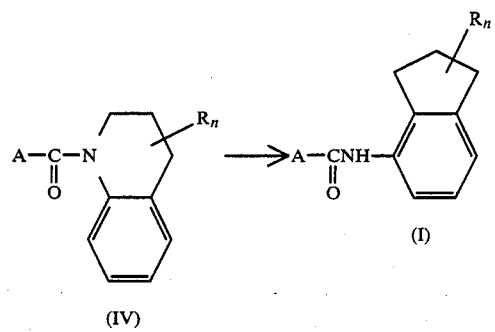

(IV)

[wherein A, R and n have the same meanings as defined above].

This reaction is carried out in rearranging acyl tetrahydroquinoline derivatives represented by the general formula (IV) in the presence of an acid catalyst at a temperature in the range of −40° to 200° C., preferably 0° to 150° C.

As examples of the acid catalyst usable for this reaction, sulfuric acid, phosphoric acid, polyphosphoric acid, and Lewis acid may be exemplified. This acid catalyst can be used in an amount in the range of from 0.001 equivalent to a large excess based on the amount of the acyl tetrahydroquinoline derivative.

The compounds of the present invention, when occasion demands, can be produced by a reaction of the following formula.

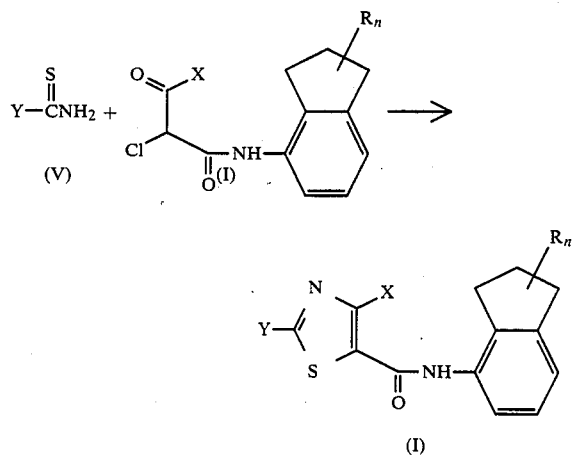

[wherein X, Y, R and n have the same meanings as defined above].

This reaction is carried out in reacting thioamide derivatives or thiourea derivatives represented by the general formula (V) with chloroacetamide derivatives represented by the general formula (VI) in the presence of an inert solvent in the reaction.

A thioamide derivative or thiourea derivative represented by the general formula (V) in this reaction is used in an amount in the range of 0.5 to 1.5 equivalent, preferably 0.9 to 1.2 equivalent based on the amount of a chloroacetamide derivative represented by the general formula (VI). This reaction can be carried out at a temperature in the range of −70° C. to the boiling point of the solvent to be used, preferably −40° C. to the boiling point of the solvent.

As examples of the solvent which is usable for the reaction, aromatic hydrocarbons such as benzene and toluene; ethers such as diethyl ether and tetrahydrofuran; polar solvents such as dimethyl sulfoxide, dimethyl formamide and water; alcohols such as methanol and ethanol; nitriles such as acetonitrile; and ketones such as acetone and methylethyl ketone may be exemplified.

The compounds of the present invention obtained as described above are novel and are excellent in fungicidal activity. It exhibits an outstanding controlling activity particularly to pathogenic fungi infesting various plants and, therefore, prove to be useful as agricultural/horticultural fungicides.

The compounds of the present invention may be used in their unaltered form as agricultural/horticultural fungicides. To ensure effective dispersion of an active ingredient on a given agricultural/horticultural field, the compounds are preferable to be used in the form of emulsifiable concentrate, wettable powder, dust, etc. incorporating suitable adjuvants as generally practiced.

As examples of the solvent, one of the agriculturally/horticulturally acceptable adjuvants used in the agricultural/horticultural fungicides of the present invention, water, alcohols such as methyl alcohol, ethyl alcohol and ethylene glycol; ketones such as acetone, methylethyl ketone and cyclohexanone; ethers such as ethyl ether, dioxane and cellosolve; aliphatic hydrocarbons such as kerosene, kerosine and fuel oil; aromatic hydrocarbons such as benzene, toluene, xylene, sorbent naphtha and methyl naphthalene; halogenated hydrocarbons such as dichloroethane, trichlorobenzene and carbon tetrachloride; acid amides such as dimethyl formamide; esters such as ethyl acetate, butyl acetate and glycerine esters of fatty acids; and nitriles such as acetonitrile may be exemplified. One member or a mixture of two or more members selected from the group of solvents enumerated above can be used.

As examples of the filler usable effectively in the fungicides, clays such as kaolin and bentonite; talcs such as talc and pyrophyllite; mineral powders such as diatomaceous earth, white carbon and other similar oxides; and plant powders such as soybean meal and carboxymethyl cellulose (CMC) may be exemplified. One member or a mixture of two or more members selected from the group of fillers enumerated above can be used.

A surfactant may be used as a filler, a dispersant, an emulsifier, or a penetrant. As examples of the surfactant to be used as such, nonionic surfactants such as polyoxyethylene alkylaryl ethers and polyoxyethylene sorbitan monolaurate; cationic surfactants such as alkyldimethylbenzyl ammonium chloride and alkyl pyridinium chloride; anionic surfactants such as alkylbenzene sulfonates, lignin sulfonates and higher alcohol sulfates; and amphoteric sufactants such as alkyl dimethyl betaine and dodecyl aminoethyl glycine may be exemplified.

One member or a mixture of two or more members selected from the group of surfactants enumerated above may be used to suit the purpose for which the surfactant is to be used.

Regarding the application of an agricultural/horticultural fungicide of the present invention, when the fungicide is to be used in the form of emulsion, a mixture obtained by combining 10 to 50 parts of the compound of the present invention, 10 to 80 parts of a solvent, and 3 to 20 parts of a surfactant is used as the formulation. Prior to use, this formulation is diluted to a prescribed concentration with water and the dilute solution is applied as by spraying, for example.

When the fungicide is to be used in the form of a wettable powder, a mixture is obtained by combining 5 to 80 parts of the compound of the present invention, 10 to 90 parts of a filler, and 1 to 20 parts of a surfactant. Prior to use, this mixture is diluted with water similar to the emulsion described above.

When the fungicide is to be used in the formulation of dust, generally a mixture obtained by homogeneously mixing 1 to 5 parts of the compound of the present invention and 95 to 99 parts of an extender such as kaoline, bentonite, or talc.

Optionally, the agricultural/horticultural fungicide may be used as mixed with other active ingredients such as fungicide, insecticide, or miticide which do not impede the fungicidal effect of the active ingredient of the fungicide.

The agricultural/horticultural fungicide of the present invention can be applied advantageously to aerial parts of plants or parts of plants submerged under water. The spray of the fungicide to the aerial parts of plants is attained generally by diluting the emulsifiable concentrate or wettable powder with water to produce an aqueous solution containing the active ingredient in a concentration of 10 to 1,000 ppm and applying this aqueous solution at a rate of 10 to 500 liters per 10 ares.

The compounds of the present invention are novel and possess an outstanding fungicidal activity. For example, they exhibit a powerful fungicidal effect to sheath blight (Rhizoctonia Solani) infesting rice, various forms of rust (Puccinia recondita) infesting wheat and snow blight (Typhula incarnata, T. ishikariensis), leaf rot (Rhizoctonia solani) infesting turf and grass, gray mold rot (Botrytis cinerea) infesting various crops, blast (Pyricularia oryzae) infesting rice, powdery mildew (Erysiphe graminis) infesting various crops, and seed rot (Sclerotinia sclerotiorum) infesting various crops. Particularly in the case of the disease of gray mold rot, the compounds of the present invention manifest extremely high activity on such fungi which are sensitive and, at the same time, resistant to benzimidazole-thiophanate fungicides and cyclic imide fungicides. Thus, they are useful as agricultural/horticultural fungicides.

Further, the compounds of the present invention possess permeability to plants and yet produce substantially no phytotoxicity on plants and show very low toxicity to men, beasts, and fishes. Thus, they are highly useful for the control of plants diseases.

The present invention will be more precisely explained while referring to Examples as follows. However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usages and conditions.

"Parts" mentioned hereinafter means "parts by weight". The compounds of the present invention synthetized in the production examples were identified as to their structure by elementary analysis, IR spectrometry, NMR spectrometry, etc.

PRODUCTION EXAMPLE 1:

Synthesis of 2amino-N-(1,1-dimethylindan-4-yl)-4-methylthiazol-5-carboxamide To 10 ml of an aqueous solution of 0.45 g (5.9 mmols) of thiourea, 10 ml of an ethanol solution of 0.95 g (3.4 mmols) of 2-aceto-2-chloro-N-(1, 1-dimethylindan-4-yl)acetamide was added and the thus obtained mixture was refluxed for 2 hours. The resultant hot reaction solution was left cooling. The cool reaction solution was alkalinized by addition of an aqueous sodium hydroxide solution to educe coarse crystals, and the coarse crystals were separated by filtration. Then, the thus obtained coarse crystals were recrystallized from ether. Thus, 0.95 g of light yellow crystals (Compound No. 1 shown in Table 4) were obtained. The yield was 93%.

Compound No. 3 shown in Table 4 was prepared by following the procedure described above, excepting 2-aceto-2 -chloro-N-(1,1,3-trimethylindan-4-yl)acetamide was used as a starting material.

PRODUCTION EXAMPLE 2

Synthesis of 2,4-dimethyl-N-(1,1,3-trimethylindan-4-yl)-thiazole-5-carboxamide To 50 ml of a benzene solution of 1.0 g (3.5 mmols) of 2-aceto-2-chloro-N-(1,1,3-trimethylindan-4-yl)-acetamide, 0.32 g (4.3 mmoles) of thioacetamide was added and the thus obtained mixture was refluxed for 1.5 hours. The resultant hot reaction solution was left cooling. The cool reaction solution was washed with a saturated brine, dried with magnesium sulfate, and concentrated under reduced pressure. The concentrated residue was separated and purified by silica gel column chromatography (eluent: ethyl acetate/hexane =½) to obtain 1.05 g of white crystals (Compound No. 2 shown in Table 4 and m.p.: 117 to 118° C.). The yield was 96%.

Compound No. 5 of the present invention shown in Table 4 was produced according to the procedure described above, excepting a different starting materials was used instead.

PRODUCTION EXAMPLE 3

Synthesis of 4-methyl-N-(1,1,3-trimethylindan-4-yl)thiazole-5-carboxamide

A mixture of 1.7 g (10.3 mmols) of 4-methyl-5-thiazole carboxylic acid and 10 ml of thionyl chloride was refluxed for 1 hour. The reaction solution was distilled under reduced pressure to remove excess thionyl chloride. The residue was dissolved in 10 ml ethyl acetate. The solution was added to 10 ml of an ethyl acetate solution of 1.8 g (10.3 mmols) of 4-amino-1,1,3-trimethylindane and 4 ml of triethylamine, and the resultant solution was stirred at room temperature for 3 hours. The solution was washed sequentially with water, aqueous sodium hydrogen carbonate solution, water, and saturated brine. The solution was dried with magnesium sulfate and then concentrated under reduced pressure. The concentrated residue was separated and purified by silica gel column chromatography (eluent: ethyl acetate/n-hexane =½), to obtain 1.6 g of amorphous solid substance (Compound No. 6 shown in Table 4). The yield was 50.2%.

Compounds No. 4 and No. 9 of the present invention shown in Table 4 were produced according to the procedure described above, excepting different starting materials were used instead.

PRODUCTION EXAMPLE 4

Synthesis of 2-mercapto-4-methyl-N-(1,1,3-trimethyl-indan-4-yl)thiazole-5-carboxamide To 10 ml of an acetone solution of 1.8 g (6 mmols) of 2-aceto-2-chloro-N-(1,1,3-trimethylindan-4-yl)acetamide, 0.75 g (6 mmols) of ammonium dithiocarbamate was added and the thus obtained mixture was stirred at room temperature for 30 minutes. Then, the mixture was refluxed for one hour. After cooling, water and ethyl acetate were added to the solution. The mixture was filtered to separate off insolubles. The organic layer was washed with a saturated brine, dried with magnesium sulfate, and then distilled under reduced pressure to remove the solvent. The obtained residue was purified by silica gel column chromatography (eluent: ethyl acetate/n-hexane=½) and then recrystallized with n-hexane-ethyl acetate, to obtain 0.8 g of light yellow crystals (Compound No. 7 shown in Table 4). The yield was 45%.

Compound No. 8 of the present invention shown in Table 4 was produced according to the procedure described above, excepting a different starting material was used instead.

TABLE 4

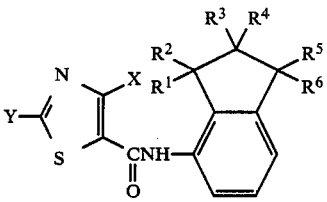

| Compound No. | X | Y | R¹ | R² | R³ | R⁴ | R⁵ | R⁶ | Physical property |
|---|---|---|---|---|---|---|---|---|---|
| 1 | $CH_3$ | $NH_2$ | H | H | H | H | $CH_3$ | $CH_3$ | m.p. 234–236° C. |
| 2 | $CH_3$ | $CH_3$ | $CH_3$ | H | H | H | $CH_3$ | $CH_3$ | NMR:δ(TMS, $CDCl_3$) 1.25(3H,s),1.36(3H,s),1.36(3H,d), 1.66(1H,dd),2.27(1H,dd),2.73(3H,s), 2.75(3H,s),3.37(1H,m),7.02(H,d), 7.30(H,t),7.36(H,br),7.78(H,d) |
| 3 | $CH_3$ | $NH_2$ | H | $CH_3$ | H | H | $CH_3$ | $CH_3$ | m.p. 258–259° C. |
| 4 | Cl | Cl | H | H | $CH_3$ | H | H | H | NMR:δ(TMS, $CDCl_3$) 1.2(3H,d),2.6(3H,m),3.1(2H,m), 7.1(H,dd),7.2(H,dd),8.2(H,br), 8.8(H,dd) |
| 5 | $CF_3$ | $CH_3$ | $CH_3$ | H | H | H | $CH_3$ | $CH_3$ | m.p. 145–147° C. |
| 6 | $CH_3$ | H | $CH_3$ | H | H | H | $CH_3$ | $CH_3$ | NMR:δ(TMS, $CDCl_3$) 1.26(3H,s),1.35(3H,d),1.36(3H,s), 1.66(H,dd),2.27(H,dd),2.83(3H,s), 3.40(H,m),7.04(H,d),7.29(H,t), 7.52(H,brs),7.75(H,d),8.81(H,s) |
| 7 | $CH_3$ | SH | $CH_3$ | H | H | H | $CH_3$ | $CH_3$ | m.p. 187–188° C. |
| 8 | $CH_3$ | $SCH_3$ | H | $CH_3$ | H | H | $CH_3$ | $CH_3$ | m.p. 96–97° C. |
| 9 | $CH_3$ | $CH_3$ | H | H | H | H | $CH_3$ | $CH_3$ | m.p. 97–99° C. |

PRODUCTION EXAMPLE 5

Synthesis of 3-chloro-N-(1,1,3-trimethylindan-4-yl)pyrazine-2-carboxamide

A mixture of 0.5 g (3.57 mmols) of 3-hydroxypyrazine-2-carboxylic acid, 3 ml of phosphorus oxychloride, and one drop of pyridine was refluxed for 3 hours. The resultant reaction solution was distilled to remove excess phosphorus oxychloride. To the residue 5 ml of ethyl acetate was added. The solution was added dropwise to 10 ml of an ethyl acetate solution of 0.53 g (3 mmols) of 4-amino-1,1,3-trimethylindane and 0.4 g (3.96 mmols) of triethylamine. The resultant mixture was stirred at room temperature for 2 hours and then sequentially washed with water, sodium hydrogen carbonate, water, and a saturated brine. The washed solution was dried with magnesium sulfate and then concentrated under reduced pressure. The concentrated residue was separated and purified by silica gel column chromatography (eluent: ethyl acetate/n-hexane=¼), to obtain 0.58 g of light yellow crystals (Compound No. 10 shown in Table 5). The yield was 61%.

Compounds Nos. 11, 12 and 13 of the present invention shown in Table 5 were produced according to the procedure described above, expecting different starting materials were used instead.

TABLE 5

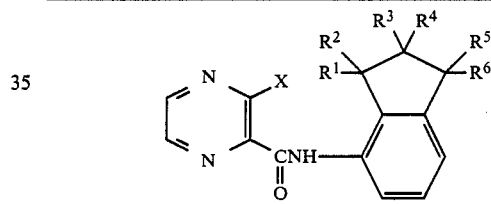

| Compound No. | X | R¹ | R² | R³ | R⁴ | R⁵ | R⁶ | Physical property |
|---|---|---|---|---|---|---|---|---|
| 10 | Cl | $CH_3$ | H | H | H | $CH_3$ | $CH_3$ | m.p. 124–125° C. |
| 11 | $CF_3$ | H | H | H | H | $CH_3$ | $CH_3$ | m.p. 143–147° C. |
| 12 | Br | H | $CH_3$ | H | H | $CH_3$ | $CH_3$ | m.p. 98–101° C. |
| 13 | $CH_3$ | H | H | $CH_3$ | H | H | H | m.p. 101–104° C. |

PRODUCTION EXAMPLE 6

Synthesis of 4-methyl-N-(1,1,3-trimethylindan-4-yl)-1,2,3-thiadiazole-5-carboxamide A mixture of 1.5 g (10.4 mmols) of 4-methyl-1,2,3-thiadiazole-5-carboxylic acid, 5 ml of thionyl chloride, and one drop of pyridine was refluxed for 1 hour. The resultant solution was distilled under reduced pressure to remove excess thionyl chloride. The obtained residue was dissolved in 10 ml of ethyl acetate. This solution was added to 10 ml of ethyl acetate solution of 1.7 g (9.7 mmols) of 4-amino-1,1,3-trimethylindane and 4 ml of triethylamine, and the resultant solution was stirred at room temperature for 3 hours. The resultant reaction solution was sequentially washed with water, aqueous sodium hydrogen carbonate solution, water, and a saturated brine, and then concentrated under reduced pressure. The concentrated residue was separated and purified by silica gel column chromatography (eluent: ethyl acetate/n-hexane=1/9), to obtain 2.17 g of white crystals (Compound No. 14 shown in Table 6). The yield was 69.1%.

Compound Nos. 15 and 16 shown in Table 6 were produced according to the procedure described above, excepting different starting materials were used instead.

PRODUCTION EXAMPLE 7

Synthesis of 2-methyl-N-(1,1,3-trimethylindan-4-yl)-3-furan carboxamide

A mixture of 1.5 g (11.9 mmols) of 2-methyl-3-furan carboxylic acid with 3 ml of thionyl chloride was refluxed for 1 hour. The reaction solution was distilled under reduced pressure to remove excess thionyl chloride. The obtained residue was cooled and 20 ml of ethyl acetate, 2 g (19.8 mmols) of triethylamine, and 1.8 g (10.3 mmols) of 1,1,3-trimethylindane-4-amine were added thereto. The resultant mixture was stirred at room temperature for 2 hours. The reaction solution was sequentially washed with water and brine. The organic layer consequently separated was dried with magnesium sulfate and then concentrated under reduced pressure. The concentrated residue was purified by being recrystallized with ethyl acetate/n-hexane, to obtain 1.8 g of white crystals (Compound No. 17 shown in Table 6). The yield was 65%.

PRODUCTION EXAMPLE 8

Synthesis of N-(1,1-dimethylindan-4-yl)-2-methyl-3-furan carboxamide 20 ml of 85% sulfuric acid solution was added to 2.5 g (9.3 mmols) of 2,2-dimethyl-N-(2-methyl-3-furan carbonyl)-1,2,3,4-tetrahydroquinoline under water cooling. The mixture was stirred at room temperature for 1 hour and then left standing overnight. Then, the reaction solution was poured into ice water and extracted from ethyl acetate. The resultant organic layer was sequentially washed with water, aqueous sodium hydrogen carbonate solution, water, and brine and then dried with magnesium sulfate. The dried mixture was concentrated. The concentrated residue was purified by being recrystallized with ethyl acetate/n-hexane, to obtain 2.1 g of white crystals (Compound No. 18 shown in Table 6). The yield was 84%.

PRODUCTION EXAMPLE 9

Synthesis of 2,5-dimethyl-N-(1,1,3-trimethylindan-4-yl)-3-furan carboxamide

A mixture of 0.6 g (4.29 mmols) of 2,5-dimethyl-3-furan carboxylic acid, 5 ml of thionyl chloride, and 1 ml of pyridine was refluxed for 1 hour. The reaction solution was distilled to remove excess thionyl chloride. The obtained residue was cooled and 15 ml of ethyl acetate, 2 ml of pyridine, and 0.75 g (4.29 mmols) of 1,1,3-trimethylidane-4-amine were added thereto. The resultant mixture was stirred at room temperature for 1 hour. The solution was sequentially washed with water, dilute hydrochloric acid, water, and brine. The solution was dried with magnesium sulfate. The residue was purified with silica gel column chromatography (eluent: ethyl acetate/n-hexane=¼), to obtain 1.0 g of white crystals (Compound No. 19 shown in Table 6). The yield was 87.4%.

Compound Nos. 21 and 22 of the present invention shown in Table 6 were produced according to the procedure described above, excepting different starting materials were used instead.

PRODUCTION EXAMPLE 10

Synthesis of 2,5-dimethyl-N-(1,1-dimethylindan-4-yl)3-furan carboxamide

To 15 ml of an ether solution of 1.5 g (8.57 mmols) of 1,1-dimethylindane-4-amine, 2 ml of N-methyl morpholine and 1.4 g (8.83 mmols) of 2,5-dimethyl-3-furan carboxylic acid chloride were added under cooling. The mixture was stirred at room temperature for 1 hour and then washed sequentially with water and brine. The solution was dried with magnesium sulfate. The resultant concentrate was purified with silica gel column chromatography (solvent for elution; ethyl acetate/n-hexane=¼), thereby obtaining 2.1 g of light yellow crystals (Compound No. 20 shown in Table 6). The yield was 85.8%.

TABLE 6

| Compound No. | A | $R^1$ | Physical property |
|---|---|---|---|
| 14 | N=N, S, CH₃ | $CH_3$ | m.p. 82–83° C. |
| 15 | N, S, CH₃ | $CH_3$ | m.p. 149–149.5° C. |
| 16 | S, N, CH₃ | H | Vitreous |
| 17 | O, CH₃ | $CH_3$ | m.p. 144–145° C. |
| 18 | O, CH₃ | H | m.p. 120–123° C. |

TABLE 6-continued

[Structure: indane ring with R¹ and two CH₃ groups at one position, A-CNH- (C=O) at another]

| Compound No. | A | R¹ | Physical property |
|---|---|---|---|
| 19 | CH₃-O-C(CH₃)=CH- (pyranone type) | CH₃ | m.p. 103–104° C. |
| 20 | CH₃-O-C(CH₃)=CH- | H | m.p. 85–88° C. |
| 21 | CH₃-O-C(CH₃)=CH- (with CH₃) | CH₃ | m.p. 105.5–106.5° C. |
| 22 | CH₃-O-C(CF₃)=CH- | CH₃ | m.p. 149–150° C. |

FORMULATION EXAMPLE 1

A wettable powder was obtained by homogeneously pulverizing and mixing 20 parts of Compound No. 1, 75 parts of diatomaceous earth, and 5 parts of a surfactant composed mainly of alkylbenzene sulfonate.

FORMULATION EXAMPLE 2

A wettable powder was obtained by homogeneously pulverizing and mixing 40 parts of Compound No. 10, 10 parts of white carbon, 47 parts of diatomaceous earth, and 3 parts of a surfactant composed mainly of polyoxyethylene alkylaryl ether sulfonate (produced by Toho Chemical Industrial Co., Ltd., Solpol 5039).

FORMULATION EXAMPLE 3

An emulsion was prepared by mixing for solution 30 parts of Compound No. 15, 15 parts of a mixture of nonionic surfactant and anionic surfactant (produced by Toho chemical Industrial Co., Ltd., Solpol 3005X), 25 parts of xylene, and 30 parts of dimethyl formamide.

FORMULATION EXAMPLE 4

A dust was obtained by mixing and pulverizing 2 parts of Compound No. 1 and 98 parts of N,N-kaoline clay (product of Tsuchiya Kaoline Co., Ltd.).

Now, test examples will be cited below to demonstrate the usefulness of the compounds of the present invention as agricultural/horticultural fungicide.

In the following examples, the compounds of the present invention will be designated by Compound Nos. shown in Tables 4, 5 and 6. The compounds used in comparative experiments are indicated by Compound Symbols shown in Table 7.

TABLE 7

| Compound symbol | Structural formula | Remark |
|---|---|---|
| A | [thiazole-substituted acrylamide with m-alkoxyphenyl] | Compound disclosed in Japanese Patent Application Laid Open (KOKAI) No. 56-57776 (1981) |
| B | [2-amino-thiazole acrylamide with phenyl] H₂N- on thiazole | Compound disclosed in Canadian Patent Disclosure No. 873,888 |
| C | 3,4-diethoxyphenyl-NHCO- group with C₂H₅O substituents | Compound disclosed in Japanese Patent Application Laid Open (KOKAI) No. 56-126856 (1983) |
| D | 3,5-dichlorophenyl dicarboximide structure (Cl, Cl on phenyl, N connected to bicyclic imide) | Commercially available fungicide designated as "Procimidone" |

TABLE 7-continued

| Compound symbol | Structural formula | Remark |
|---|---|---|
| E | (structure: HS-C(S)=C(N=)CH₃ with -C(=O)NH-phenyl) | Compound disclosed in DE No. 2,132,392 |
| F | (structure: 2-CF₃-phenyl-O-NH-C(=O)- linked to 1,1-dimethylindane) | Compound disclosed in Japanese Patent Application Laid Open (KOKAI) No. 58-140054 (1983) |
| G | (structure: CH₃-substituted pyranone with -C(=O)NH-phenyl) | Compound disclosed in German Patent Application (Offenlegungsschrift) No. 2,922,292 |

TEST EXAMPLE 1

Preventive test against sensitive strain of *Botrytis cinerea* on cucumber

To cucumbers (species: Yotsuba) nursed in pots 6 cm in diameter to the cotyledonal stage, the wettable powder prepared by following the procedure of Formulation Example 1 and diluted with water to a prescribed concentration, was applied by spraying on the aerial parts at a ratio of 10 ml per pot. After the applied solution was air dried, a drug-sensitive strain of *Botrytis cinerea* was inoculated by spraying to the aereal parts of the cucumbers. The cucumbers were kept in a moist chamber at 23° C. for four days. Then, the cucumbers were examined for possible sign of disease contraction. This examination was carried out as follows. The degree of disease contraction was determined by measuring ratio of disease areas of sample leaves, classifying the ratio by the index numbers 0, 1, 3 and 5, assigning numbers of disease leaves to respective index numbers, $n_0$, $n_1$, $n_3$, and $n_5$, and calculating the following formula using the results of assignment (n represents total number of sample leaves involved).

| Index of disease contraction | Ratio of disease area |
|---|---|
| 0 | Absence of disease contraction |
| 1 | Disease area up to about ¼ of total leaf surface |
| 3 | Disease area between ¼ and ½ of total leaf surface |
| 5 | Disease area of not less than ½ of total leaf surface |

$$\text{Degree of disease contraction} = \frac{0 \times n_0 + 1 \times n_1 + 3 \times n_3 + 5 \times n_5}{n}$$

Preventive value was calculated in accordance with following formula.

$$\text{Preventive value (\%)} = \frac{\left(\begin{array}{c}\text{Degree of disease}\\\text{contraction in}\\\text{untreated plot}\end{array}\right) - \left(\begin{array}{c}\text{Degree of disease}\\\text{contraction in}\\\text{treatment plot}\end{array}\right)}{\left(\begin{array}{c}\text{Degree of disease contraction}\\\text{in untreated plot}\end{array}\right)} \times 100$$

The results were as shown in Table 8.

TABLE 8

| Compound No. | Concentration of active ingredient (ppm) | Preventive value (%) |
|---|---|---|
| 1 | 500 | 100 |
| 2 | 500 | 100 |
| 3 | 500 | 100 |
| 4 | 500 | 100 |
| 6 | 500 | 100 |
| 7 | 500 | 100 |
| 10 | 500 | 100 |
| 11 | 500 | 100 |
| 12 | 500 | 100 |
| 15 | 500 | 100 |
| 17 | 500 | 100 |
| 19 | 500 | 100 |
| A | 500 | 0 |
| B | 500 | 0 |
| C | 500 | 0 |
| E | 500 | 0 |
| F | 500 | 0 |
| G | 500 | 0 |

TEST EXAMPLE 2

Preventive test against resistant strain of *Botrytis cinerea* on cucumber

To cucumbers (species: Yotsuba) nursed in pots 6 cm in diameter to the cotyledonal stage, the wettable powder prepared by following the procedure of Formulation Example 1 and diluted with water to a prescribed concentration, was applied by spraying on the aerial parts at a ratio of 10 ml per pot. After the applied solution was air dried, a drug-resistant strain of *Botrytis* cinerea was inoculated by spraying to the aereal parts of the cucumbers. The cucumbers were kept in a moist chamber at 23° C. for four days. Then, the cucumbers were examined for possible sign of disease contraction. This examination was carried out as follows. The degree of disease contraction was determined by measuring ratio of disease areas of sample leaves, classifying the ratio by the index numbers 0, 1, 3 and 5, assigning numbers of disease leaves to respective index numbers, $n_0$, $n_1$, $n_3$, and $n_5$, and calculating the following formula using the results of assignment (n represents total number of sample leaves involved).

| Index of disease contraction | Ratio of disease area |
|---|---|
| 0 | Absence of disease contraction |
| 1 | Disease area up to about ¼ of total leaf surface |
| 3 | Disease area between ¼ and ½ of total leaf surface |
| 5 | Disease area of not less than ½ of total leaf surface |

$$\text{Degree of disease contraction} = \frac{0 \times n_0 + 1 \times n_1 + 3 \times n_3 + 5 \times n_5}{n}$$

Preventive value was calculated in accordance with the following formula.

Preventive value (%) =

$$\frac{\left(\begin{array}{c}\text{Degree of disease}\\\text{contraction in}\\\text{untreated plot}\end{array}\right) - \left(\begin{array}{c}\text{Degree of disease}\\\text{contraction in}\\\text{treatment plot}\end{array}\right)}{\left(\begin{array}{c}\text{Degree of disease contraction}\\\text{in untreated plot}\end{array}\right)} \times 100$$

The results were as shown in Table 9.

TABLE 9

| Compound No. | Concentration of active ingredient (ppm) | Preventive value (%) |
|---|---|---|
| 1 | 500 | 100 |
| 2 | 500 | 100 |
| 3 | 500 | 100 |
| 4 | 500 | 100 |
| 6 | 500 | 100 |
| 7 | 500 | 100 |
| 10 | 500 | 100 |
| 11 | 500 | 100 |
| 12 | 500 | 100 |
| 15 | 500 | 100 |
| 17 | 500 | 100 |
| 19 | 500 | 100 |
| A | 500 | 0 |
| B | 500 | 0 |
| D | 500 | 0 |
| E | 500 | 0 |
| F | 500 | 0 |
| G | 500 | 0 |

TEST EXAMPLE 3

Preventive test against Erysiphe graminis on wheat

To wheat plants (species: Norin No. 61) nursed in pots 6 cm in diameter to the 1- to 2-leaf stage, a wettable powder prepared by following the procedure of Formulation Example 1 and diluted with water a prescribed concentration, was applied by spraying to aereal parts of plants at a ratio of 10 ml per pot. After the applied solution was air dried, a suspension of spores obtained from wheat leaves which had contracted powdery mildew (Erysiphe graminis) was inoculated by spraying. The wheat plants were left standing at room temperature for 7 to 10 days.

The effect of control was rated by measuring ratio of disease surfaces of sample leaves and calculating a preventive value in accordance with the following formula using the values obtained by the measurement. The results were as shown in Table 10.

TABLE 10

| Compound No. | Concentration of active ingredient (ppm) | Preventive value (%) |
|---|---|---|
| 1 | 500 | 100 |
| 2 | 500 | 100 |
| 3 | 500 | 100 |
| 4 | 500 | 100 |
| 7 | 500 | 100 |

TEST EXAMPLE 4

Preventive test against Rizoctonia solani on rice

To rice plants (species: Nipponbare) nursed in pots 6 cm in diameter to the 3- to 4-leaf stage, a wettable powder prepared by following the procedure of Formulation Example 1 and diluted with water to a prescribed concentration, was applied by spraying to aereal parts of plants at a ratio of 10 ml per pot. After the applied solution was air dried, a suspension of hyphae of sheath blight (Rhizoctonia solani) culture in a YG medium was inoculated by spraying. The rice plants were left standing in a moist room at 29° C. for 40 hours and then left standing at rest in a water tank at room temperature for 3 days. The effect of control was rated by measuring disease spots as degree of disease contraction and determining a control index in accordance with the following formula using the values obtained by the measurement. The results were as shown in Table 11.

Preventive value (%) =

$$\frac{\left(\begin{array}{c}\text{Disease contraction}\\\text{index per leaf in}\\\text{untreated plot}\end{array}\right) - \left(\begin{array}{c}\text{Disease contraction}\\\text{index per leaf in}\\\text{treatment plot}\end{array}\right)}{\left(\begin{array}{c}\text{Disease contraction}\\\text{index per leaf in}\\\text{untreated plot}\end{array}\right)} \times 100$$

TABLE 11

| Compound No. | Concentration of active ingredient (ppm) | Preventive value (%) |
|---|---|---|
| 2 | 500 | 100 |
| 15 | 500 | 100 |
| 17 | 500 | 100 |
| 18 | 500 | 100 |
| 19 | 500 | 100 |
| 20 | 500 | 100 |
| 22 | 500 | 100 |

TEST EXAMPLE 5

Preventive test against Puccinia recondita on wheat

To wheat plants (species: Norin No. 61) nursed in pots 6 cm in diameter to the 1- to 2-leaf stage, a wettable powder prepared by following the procedure of Test Example 1 and diluted with water to a prescribed concentration, was applied to aereal parts of the wheat plants at a ratio of 10 ml per pot. After the applied solution was air dried, a suspension of spores obtained by grinding wheat which had contracted brown rust (Puccinia recondita) was inoculated by spraying. The wheat plants were kept in a moist chamber at 22° C. for 15 hours and then left standing in a glass house at room temperature for 7 days.

The control effect was rated by measuring ratios of disease spot areas of the leaves and calculating a preventive value in accordance with the following formula using the values found by the measurement.

The results were as shown in Table 12.

Preventive value (%) =

$$\frac{\left(\begin{array}{c}\text{Average ratio of}\\\text{disease spot area}\\\text{in untreated plot}\end{array}\right) - \left(\begin{array}{c}\text{Average ratio of}\\\text{disease spot area}\\\text{in treatment plot}\end{array}\right)}{\left(\begin{array}{c}\text{Average ratio of disease}\\\text{spot area in untreated}\\\text{plot}\end{array}\right)} \times 100$$

TABLE 12

| Compound No. | Concentration of active ingredient (ppm) | Preventive value (%) |
| --- | --- | --- |
| 1 | 500 | 100 |
| 2 | 500 | 100 |
| 3 | 500 | 100 |
| 4 | 500 | 100 |
| 5 | 500 | 100 |
| 6 | 500 | 100 |
| 7 | 500 | 100 |
| 10 | 500 | 100 |
| 11 | 500 | 100 |
| 12 | 500 | 100 |
| 13 | 500 | 100 |
| 14 | 500 | 100 |
| 15 | 500 | 100 |
| 16 | 500 | 100 |
| 17 | 500 | 100 |
| 18 | 500 | 100 |
| 19 | 500 | 100 |
| 20 | 500 | 100 |
| 21 | 500 | 100 |
| 22 | 500 | 100 |

What is claimed is:

1. An N-indanyl carboxamide compound having the formula (I):

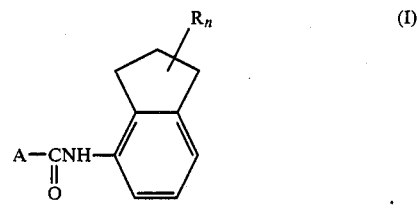

wherein A represents a group of the formula:

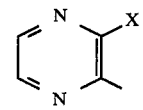

wherein X represents halogen, methyl or trifluoromethyl; Y represents hydrogen, halogen, lower alkyl, amino, mercapto or lower alkylthio; $R^1$ represents methyl or trifluoromethyl; and $R^2$ and $R^3$ independently represents hydrogen or methyl; R represents lower alkyl and n represents an integer of 1 to 6.

2. An agricultural/horticultural fungicide composition, comprising as an active ingredient an effective amount of an N-indanyl carboxamide compound having the formula (I):

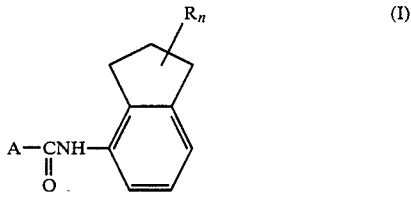

wherein A represents a group of the formula:

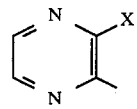

wherein X is halogen, methyl or trifluoromethyl; Y is hydrogen, halogen, lower alkyl, amino, mercapto or lower alkylthio; $R^1$ is methyl or trifluoromethyl; and $R^2$ and $R^3$ independently represents hydrogen or methyl; R represents lower alkyl and n represents an integer in the range of 1 to 6; and a suitable excipient.

* * * * *